United States Patent [19]
Rissmaney et al.

[11] Patent Number: 5,957,959
[45] Date of Patent: Sep. 28, 1999

[54] HOME TANNING APPARATUS

[76] Inventors: Pouran Rissmaney; David J. Hansen, both of 9637 El Clair Ranch Rd., Boynton Beach, Fla. 33437

[21] Appl. No.: 09/055,519

[22] Filed: Apr. 6, 1998

[51] Int. Cl.[6] .................................................. A61N 5/01
[52] U.S. Cl. .................................... 607/88; 250/494.1
[58] Field of Search ............................. 607/88, 90–91, 607/94, 81; 250/494.1, 455.11, 504 R

[56] References Cited

U.S. PATENT DOCUMENTS

| | | |
|---|---|---|
| 1,048,858 | 12/1912 | Murray . |
| 1,064,983 | 6/1913 | Murray et al. . |
| 2,631,588 | 3/1953 | Paschell . |
| 4,277,855 | 7/1981 | Poss . |
| 4,444,189 | 4/1984 | Seiverd . |
| 4,469,102 | 9/1984 | Fish . |
| 4,582,062 | 4/1986 | Albini . |
| 4,663,787 | 5/1987 | Kolsch . |
| 4,683,886 | 8/1987 | Kramer et al. . |
| 4,740,707 | 4/1988 | Thaw . |
| 4,984,571 | 1/1991 | Springer, Jr. et al. . |
| 5,370,673 | 12/1994 | Angelo . |

*Primary Examiner*—Linda C. M. Dvorak
*Assistant Examiner*—Roy Gibson
*Attorney, Agent, or Firm*—Chase & Yakimo, L.C.

[57] ABSTRACT

A tanning apparatus includes a plurality of tubular lamp housings releasably joined together in an electrical series relationship for tanning either an erect or recumbent person. Lamp housings, walls, and power cords are easily attachable and detachable for adjusting the configuration of the apparatus. Each lamp housing includes an ultraviolet lamp, ballast, and igniter. The lamp housing further includes a front panel which allows access to the lamp for replacement while protecting a user from injury in case a lamp bursts during use. The front panel is transparent, allowing ultraviolet rays to be transmitted toward a user. Reflective surfaces within the lamp housings and on the interior wall surfaces further contribute to efficient tanning. A frame is provided to support the apparatus above a recumbent user. The lamp housings may also be vertically positioned to surround and tan an erect user. Following use, the apparatus may be rolled into a compact bundle and secured by straps for transport or storage.

20 Claims, 8 Drawing Sheets

HOME TANNING APPARATUS

BACKGROUND OF THE INVENTION

This invention relates to tanning apparatuses and, more particularly, to a home tanning apparatus which is adaptable to tan a person standing up or lying down and which is collapsible into a compact bundle for transport or storage.

The desire to maintain a healthy looking physique is evidenced by the continued vitality of health and fitness facilities. Further, maintenance of evenly tanned skin is viewed as an important aspect of physical fitness and beauty by many people. Tanning beds and booths have therefore become a standard fixture in fitness facilities, beauty salons, etc. Commercial tanning devices, however, are extremely expensive - a cost that is passed on to consumers of tanning services. Commercial tanning beds and booths such as those disclosed in U.S. Pat. Nos. 4,683,886 and 4,469,102 to Kramer and Fish, respectively, may range from $3,000 to $7,000 per unit.

The expense of commercial tanning services combined with the inconvenience of travelling to and from a tanning facility on a regular basis has fostered a desire to tan at home. Accordingly, several tanning devices for home use have been proposed in the prior art. In U.S. Pat. No. 4,582,062 to Albini, a tent structure having reflective interior surfaces and a single sunlamp is proposed for tanning a portion of a person lying within the tent. A booth-type tanning device is disclosed in U.S. Pat. No. 4,984,571 which is collapsible for storage against a wall.

Although assumably effective in operation, such devices are still disadvantageous for home use. Although the tent structure of '062 is collapsible for out-of-the-way storage, it includes numerous components that must be assembled together for use and then separated for storage. The device is therefore inefficient, inconvenient, and susceptible to lost or damaged parts. The collapsible tanning booth of '571 is also disadvantageous for home use in that it occupies a prominent upright position within a room even when collapsed for storage.

Thus, it is desirable to have an apparatus which is adaptable to provide efficient tanning to an individual in either a standing or lying position within a residential environment. It is also desirable to have a tanning apparatus which is lightweight and flexible for collapsing into a compact bundle for transport or storage.

SUMMARY OF THE INVENTION

In response thereto, we have invented a tanning apparatus which includes a plurality of tubular housings, each housing having an ultraviolet lamp, ballast, and igniter. The housings are joined together by lightweight, flexible walls except that the first and last housings are not joined together. The flexible walls allow the apparatus to stand vertically to encircle a standing person or to overlay a horizontal frame. Lamp housings and flexible walls are easily attachable and detachable for adjusting the length of the apparatus as desired by a user. Base plates may be placed on the lower end of each housing for stability when the apparatus is vertically oriented. Thus, the apparatus is adaptable to tan a person who is standing or lying down.

The interior surfaces of the walls are made of reflective material which reflect ultraviolet rays toward the individual within or beneath the apparatus, contributing to a faster and more complete tan. Flexible walls having various exterior surfaces are easily substituted according to the decor of a room. Power is carried from housing to housing through detachable wires mounted within hemmed edges in the flexible walls. Each housing also includes a transparent panel in front of each lamp which allows ultraviolet rays to pass through while protecting a user from injury in case the lamp bursts.

The flexible walls which join the housings also provide a convenient storage mechanism for the apparatus. Following use, the tanning apparatus may be laid horizontally upon the floor, rolled into a compact bundle, and secured by straps. Accordingly, the entire apparatus may be quickly and conveniently transported, erected, or stored in a small space as a single unit.

It is therefore a general object of this invention to provide a tanning apparatus which is convenient to use and store in a residential home environment.

Another object of this invention is to provide a tanning apparatus, as aforesaid, having a plurality of ultraviolet lamps and interior reflective surfaces for providing an evenly distributed tan to a user.

A further object of this invention is to provide a tanning apparatus, as aforesaid, having attachable/detachable housings, walls, and wires, for adapting to tan a person who is standing or lying down.

A still further object of this invention is to provide a tanning apparatus, as aforesaid, having a lightweight and flexible material which joins a plurality of lamp housings.

Still another object of this invention is to provide a tanning apparatus, as aforesaid, which can be quickly rolled up into a compact bundle and secured for transport or storage.

Yet another object of this invention is to provide a tanning apparatus, as aforesaid, having exterior surfaces of variable decoration.

A particular object of this invention is to provide a tanning apparatus, as aforesaid, having a shield about each ultraviolet lamp to protect a user from injury in case of lamp explosion.

Other objects and advantages of this invention will become apparent from the following description taken in connection with the accompanying drawings, wherein is set forth by way of illustration and example, embodiments of this invention.

DESCRIPTION OF THE PREFERRED EMBODIMENT

Figure 1:
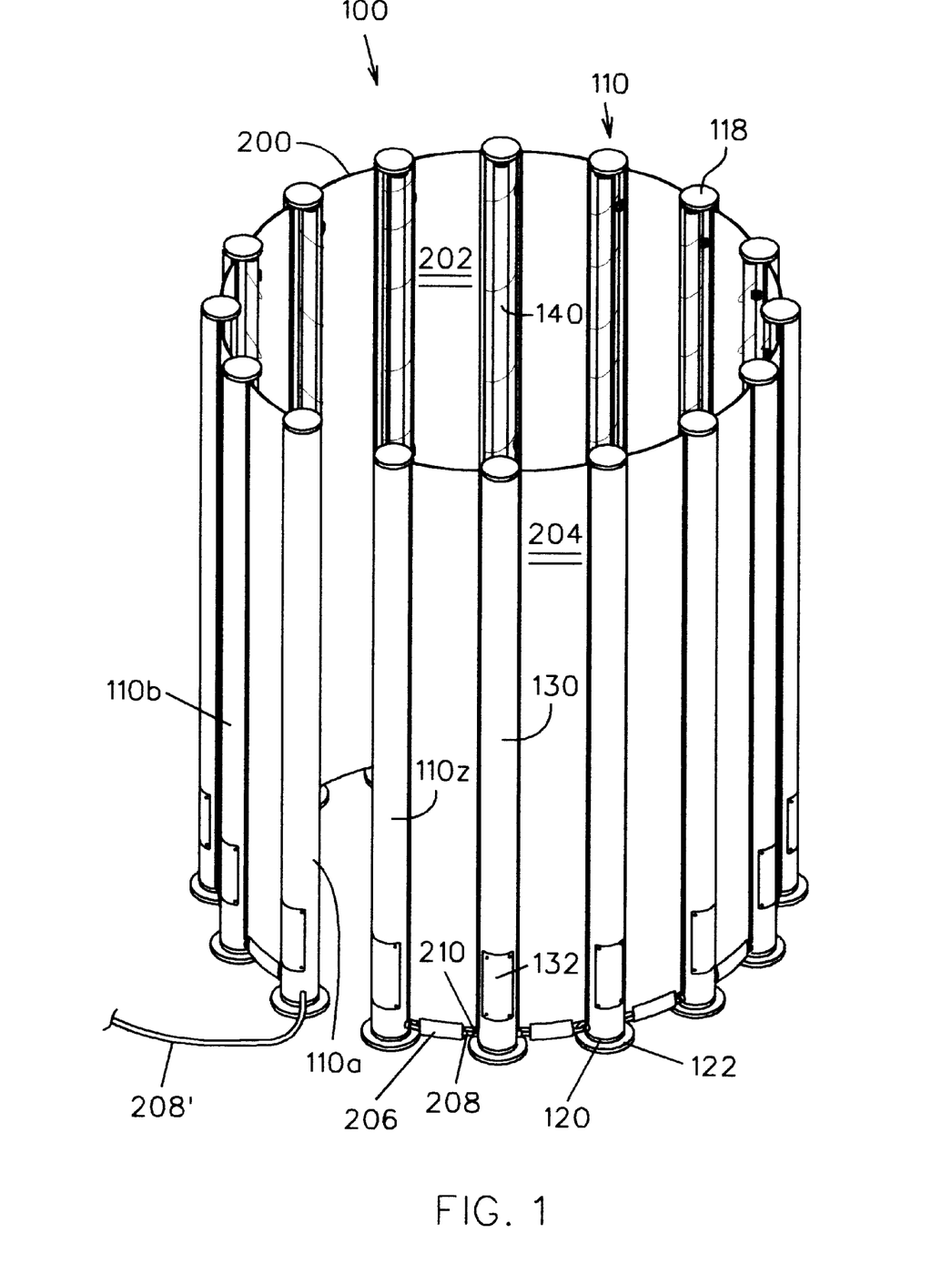
FIG. 1 is a perspective view of the apparatus of the present invention.
Figure 2:
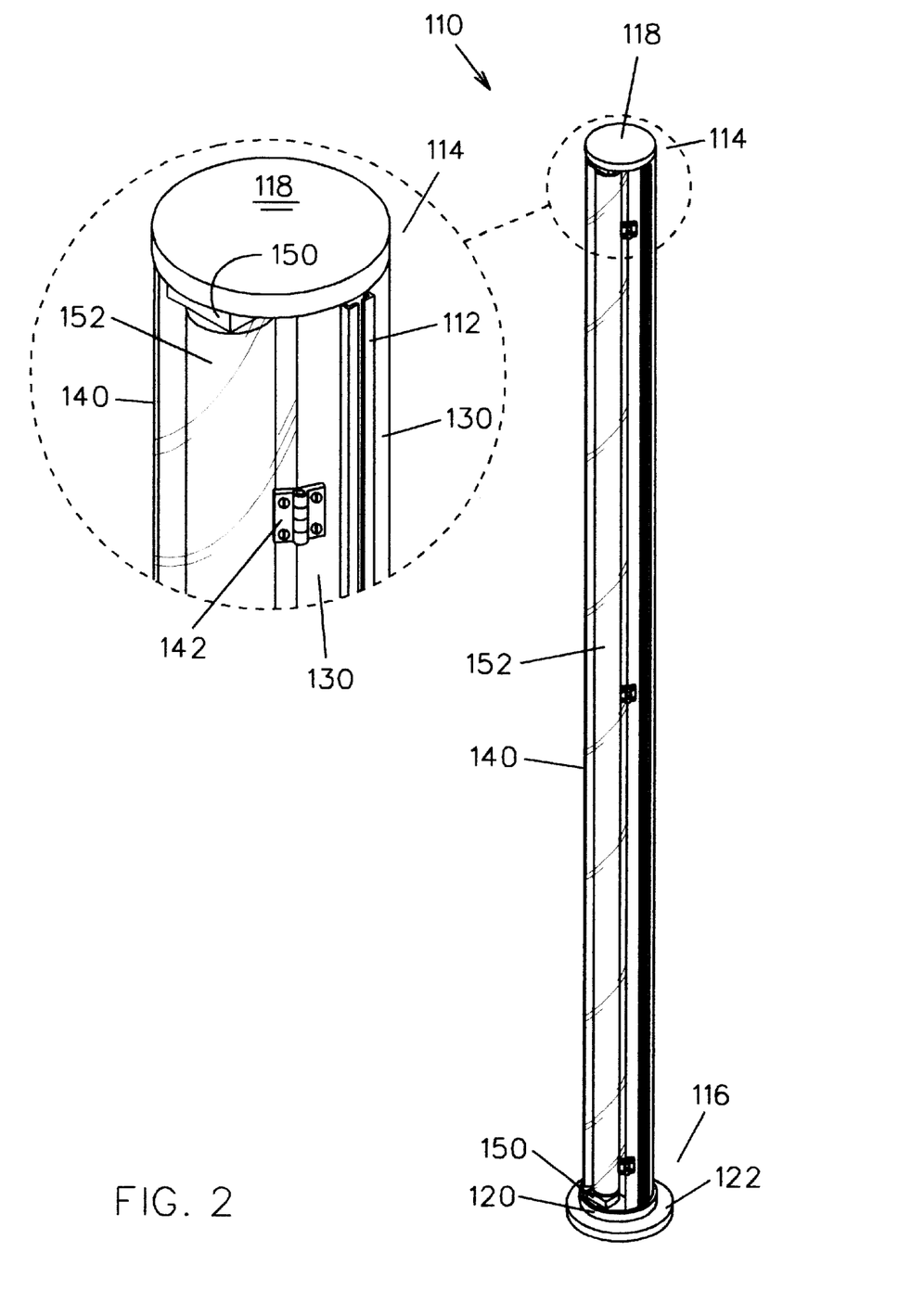
FIG. 2 is a perspective view of an ultraviolet lamp housing with an enlarged isolated view of an upper end of the housing.
Figure 8:
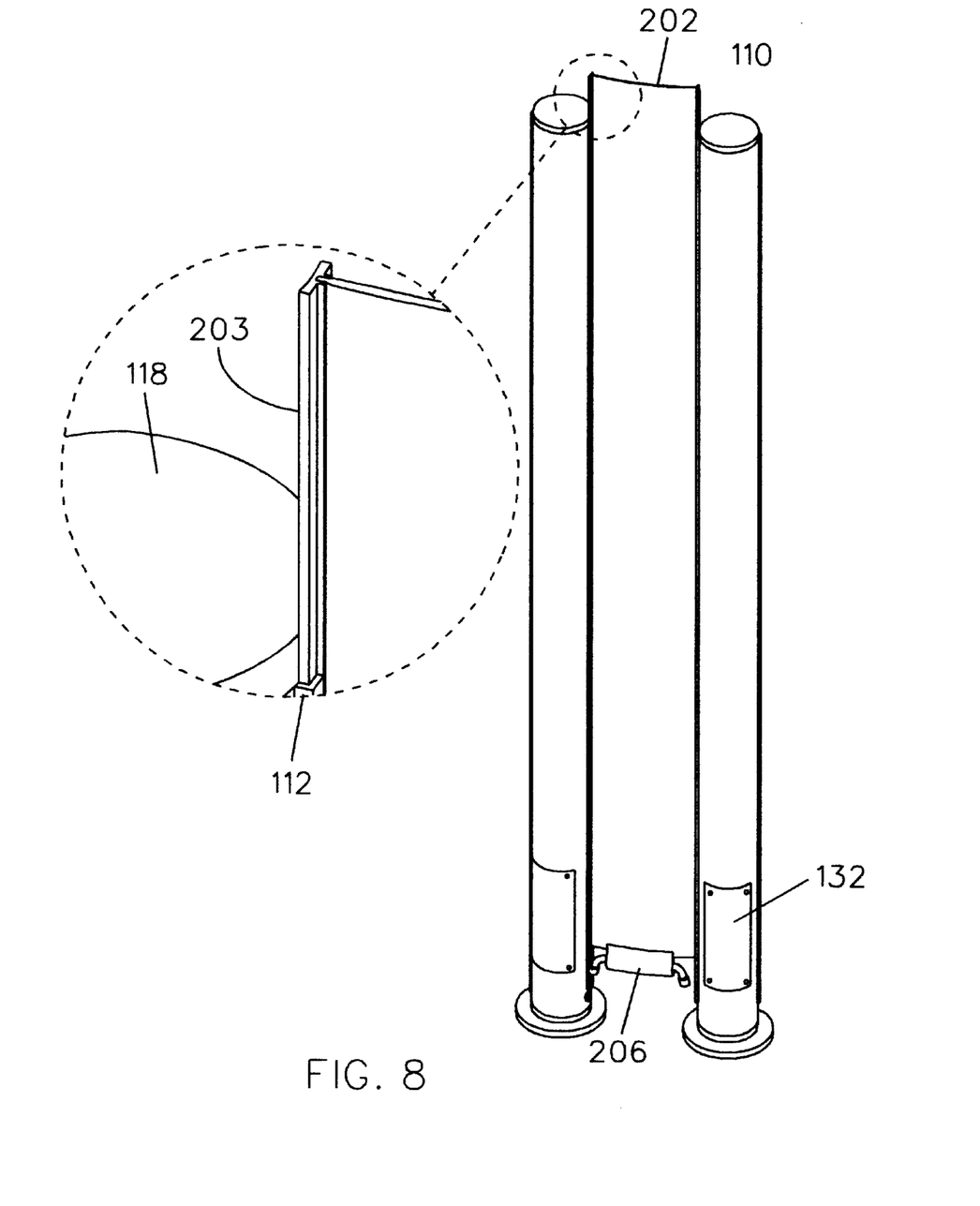
FIG. 8 is a fragmentary view of a wall panel showing the edge configuration for engagement within a housing channel.

Turning more particularly to the drawings, FIG. 1 shows the preferred embodiment of the tanning apparatus 100 having a plurality of elongated tubular lamp housings 110 situated in an upright position for tanning a standing person. A first housing 110a is joined to the next housing 110b and so on in an in-line spaced apart relationship by lightweight, flexible walls 200, the walls 200 having a reflective interior surface 202 and a decorative exterior surface 204. Each wall 200 is releasably joined to adjacent housings 110 by slidable insertion of the wall 200 ends into elongated channel/flange structures 112 integrally attached to the sides of the lamp housings 110 (FIG. 2). The ends 203 of each wall 200 may be a straight edge or a configuration complementary to the interior of each channel 112 (FIG. 8). Walls 200 are thus slidably removable for replacement with walls of different exterior decoration. In like manner, the number of lamp housings 110 may be varied to facilitate tanning while lying down as will be described later.

Each flexible wall 200 includes a hemmed lower edge 206 having a supplemental power cord 208 secured therein, said cords 208 carrying electrical power in series from the primary cord 208' and between adjacent lamp housings 110. Primary cord 208' extends from the initial housing 110a for connection to an electrical power source. Each power cord 208 includes a pair of electrical plugs 210 integrally attached thereto at opposing ends thereof for releasably engaging electrical sockets 150 presented near lower ends 116 of each housing 110. A power cord 208 may be disengaged in conjunction with detachment of a wall 200 or lamp housing 110.

Figure 3A:
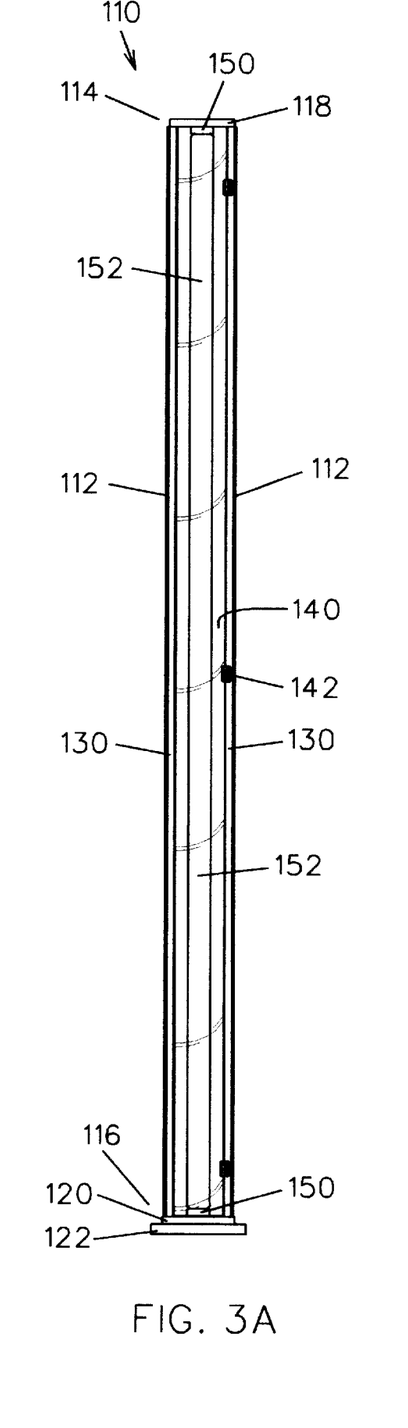
FIG. 3A is a front view of the lamp housing of FIG. 2.
Figure 3B:
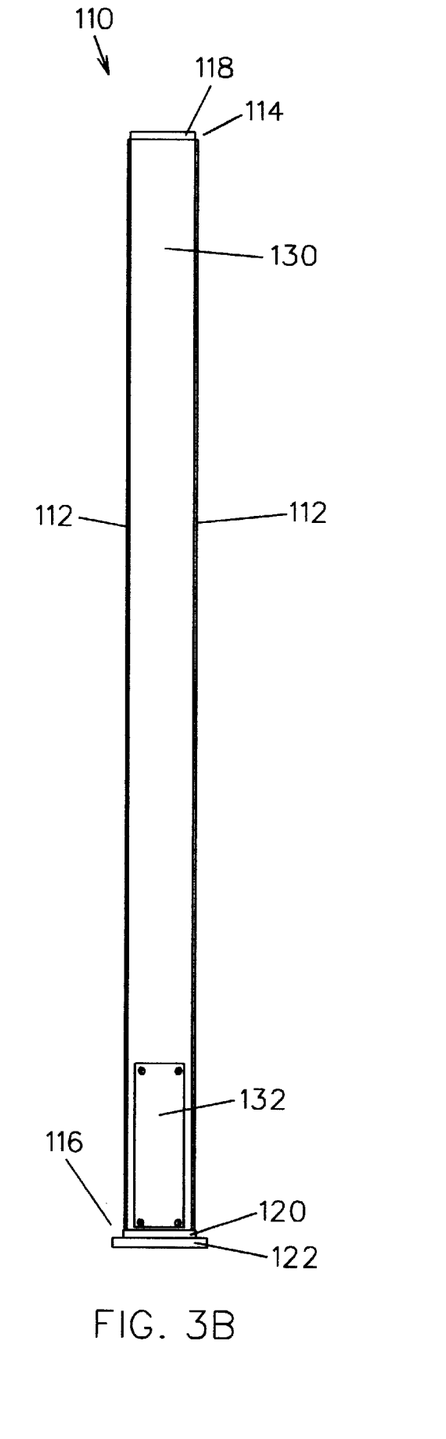
FIG. 3B is a rear view of the lamp housing of FIG. 2.
Figure 4A:
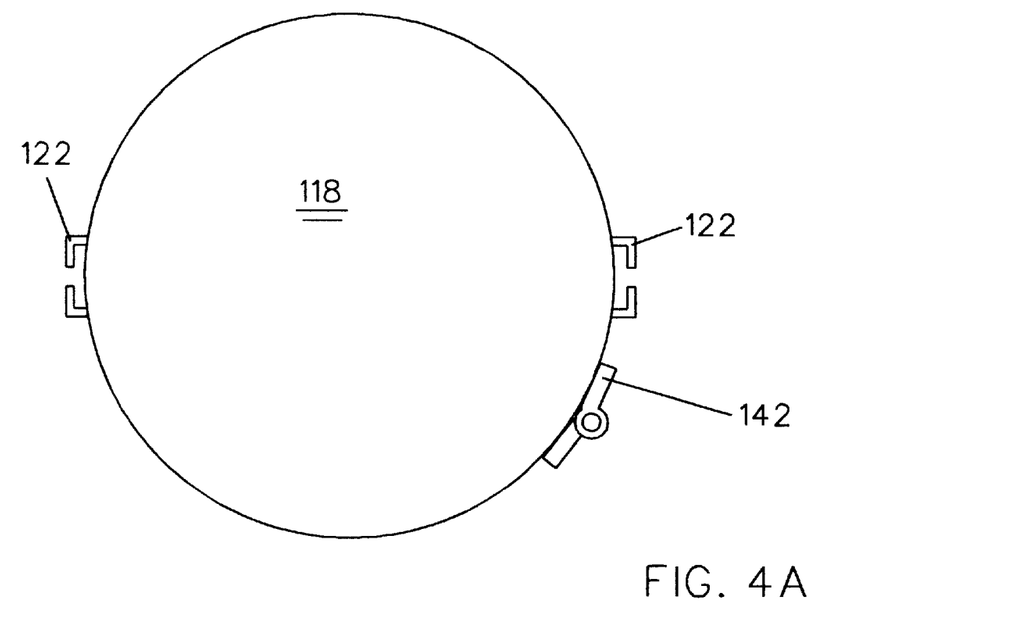
FIG. 4A is a top view of the lamp housing of FIG. 2 with the top cap attached.
Figure 4B:
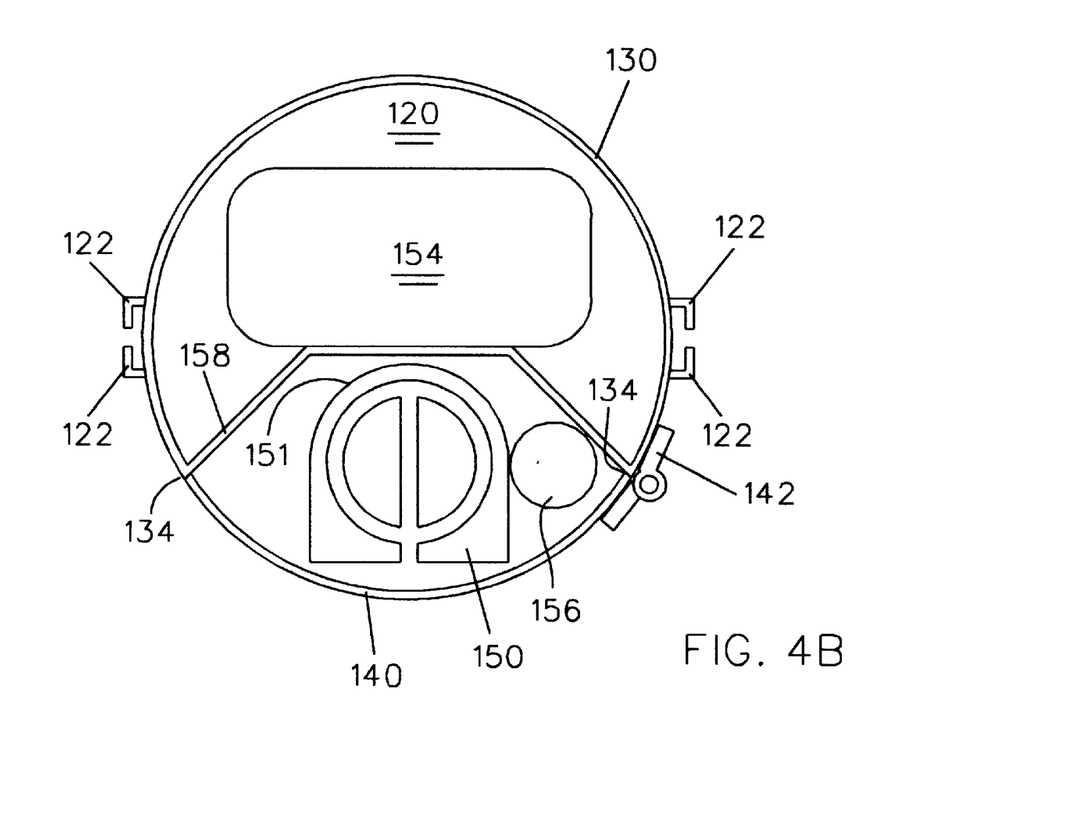
FIG. 4B is a top view of the lamp housing of FIG. 2 with the top cap removed.

As shown in FIGS. 2–4, a lamp housing 110 includes a generally hemispherical rear panel 130 (FIG. 3B) preferably made of a hard plastic material for protecting the apparatus from damage, particularly during storage. The rear panel 130 includes a subpanel 132 removably attached near the lower end 116 thereof for providing access to inner components (FIG. 4A). A lamp housing 110 further includes an elongated front panel 140 pivotably attached to the rear panel 130 with hinges 142 (FIG. 2) which provides access to the interior of the housing 110 for maintenance or replacement of a lamp. The front panel 140 is preferably constructed of a transparent acrylate resin such as Plexiglass® which allows transmission of ultraviolet rays therethrough while protecting a user from injury if a lamp bursts during use.

A lamp housing 110 further includes top 118 and bottom 120 covers fixedly attached to upper 114 and lower 116 ends thereof. A base plate 122 may be removably attached to each bottom cover 120 for increasing the stability of the lamp housings 110, the base plate 122 having a greater circumference than a bottom cover 120. Conventional lamp sockets 150 are interiorly fixedly attached to top 118 and bottom 120 covers for holding an ultraviolet lamp 152. The bottom cover 120 further includes a ballast 154 and igniter 156 for activating an ultraviolet lamp 152 (FIG. 4A). Each housing 110 further includes a partition 158 extending between top 118 and bottom 120 covers and integrally attached thereto at junctures 134 between front 140 and rear 130 panels, said partition 158 angularly extending about a rear side 151 of the lamp sockets 150 for reflecting ultraviolet rays through the front panel 140.

As shown in FIG. 1, the housings 110 surround a user upon the first housing 110a being positioned next to terminal housing 110z. As such these initial and terminal housings need not have channel structures 112 on both sides of the housing 110. Alternatively, these housings may have channels 112 on both sides thereof with or without a wall extending therebetween. The wall between housing 110a, 110z may be inserted by the user upon the user entering the housing enclosure. The flexibility of the wall panels 200 and the manner of attachment of the wall panel edges to the channels 112 allowing for a variable positioning of the housings about or encircling the user.

Figure 5:
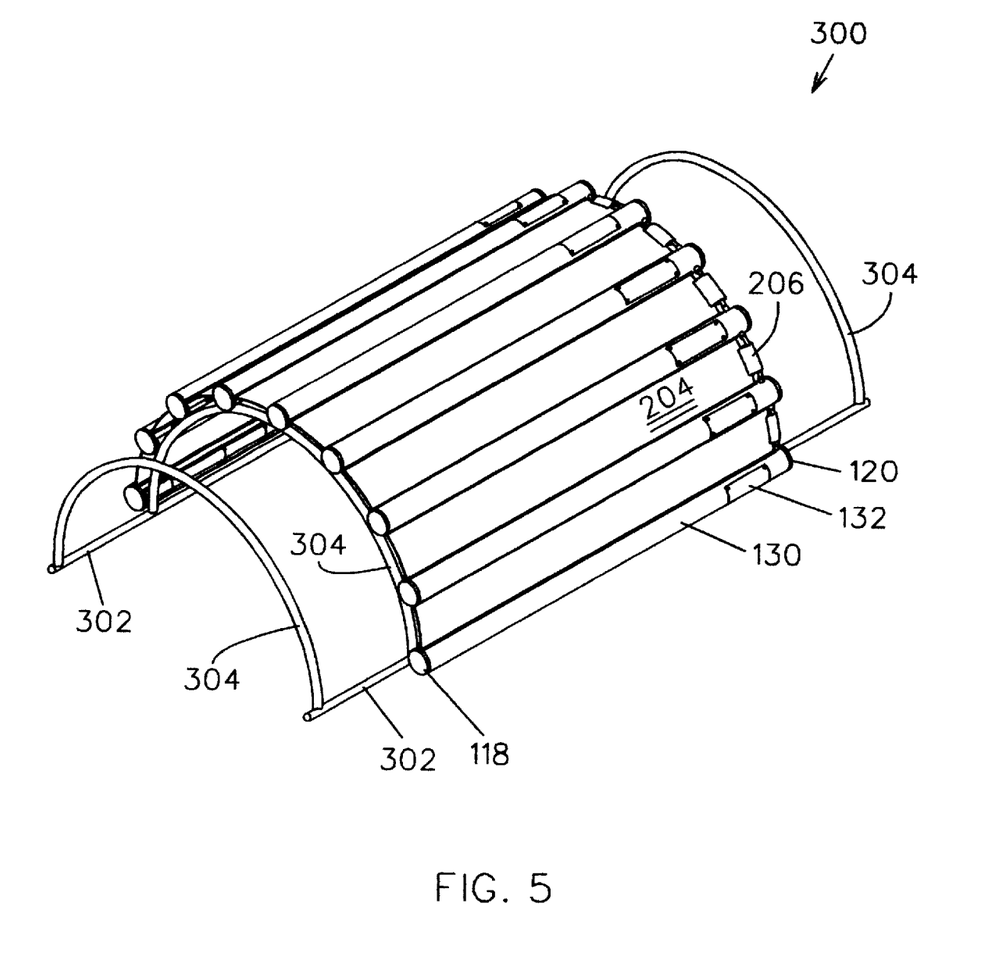
FIG. 5 is a perspective view of the apparatus of FIG. 1 in a horizontal position upon a frame with some lamp housings removed according to the invention.

Turning to FIG. 5, the apparatus 100 may alternatively be laid horizontally upon a support frame 300 for tanning a recumbent person thereunder following detachment of a number of lamp housings 110 as described above. The frame 300 includes a pair of spaced apart parallel rods 302 integrally attached to a plurality of spaced apart arched rods 304 spanning said parallel rods 302. It is understood that while the support frame 300 is generally the length of an adult person, the apparatus 100 itself can be laterally positioned upon the frame as desired by a user.

Figure 6:
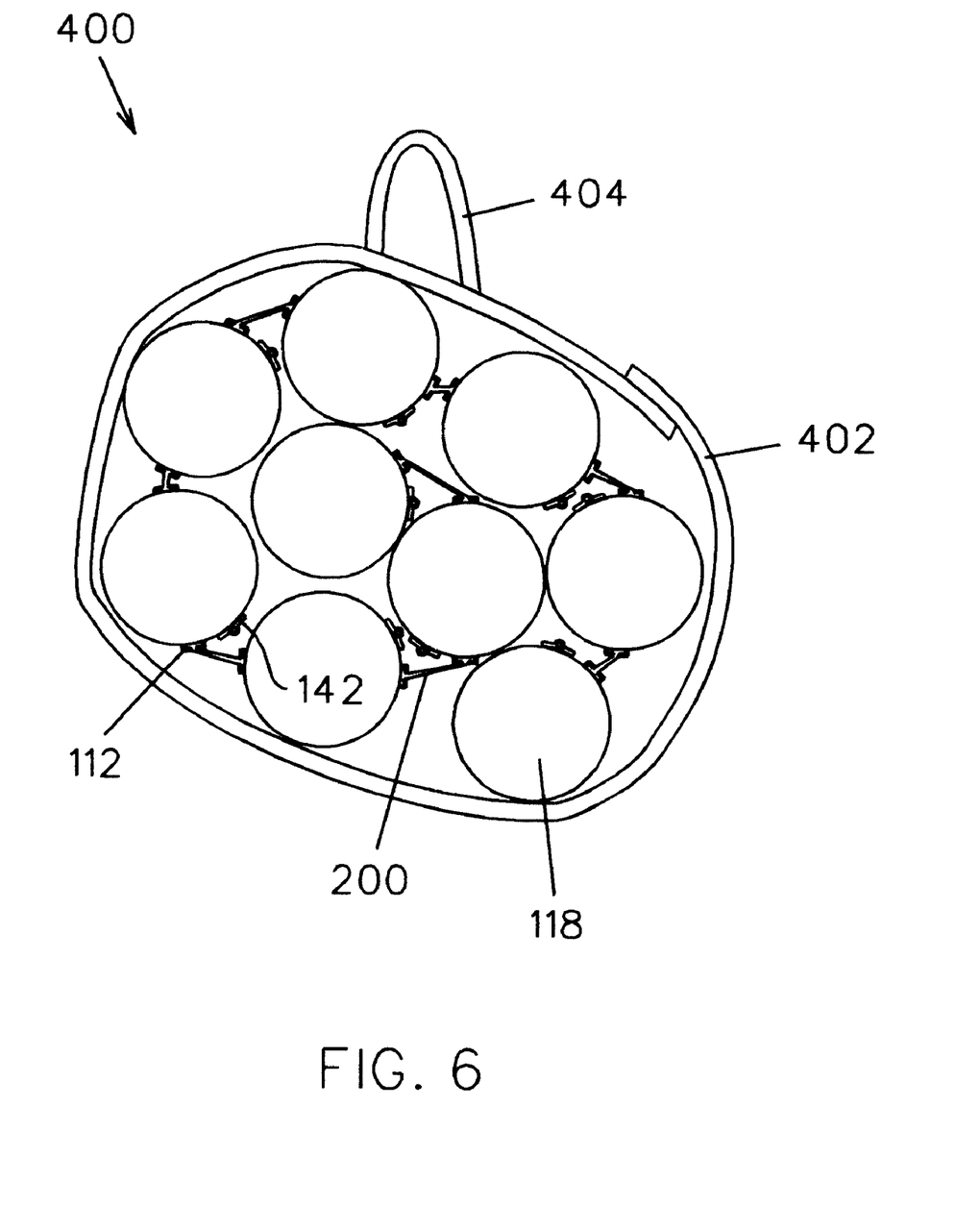
FIG. 6 is a top view of the apparatus of FIG. 5 in a rolled-up position within encompassing straps.
Figure 7:
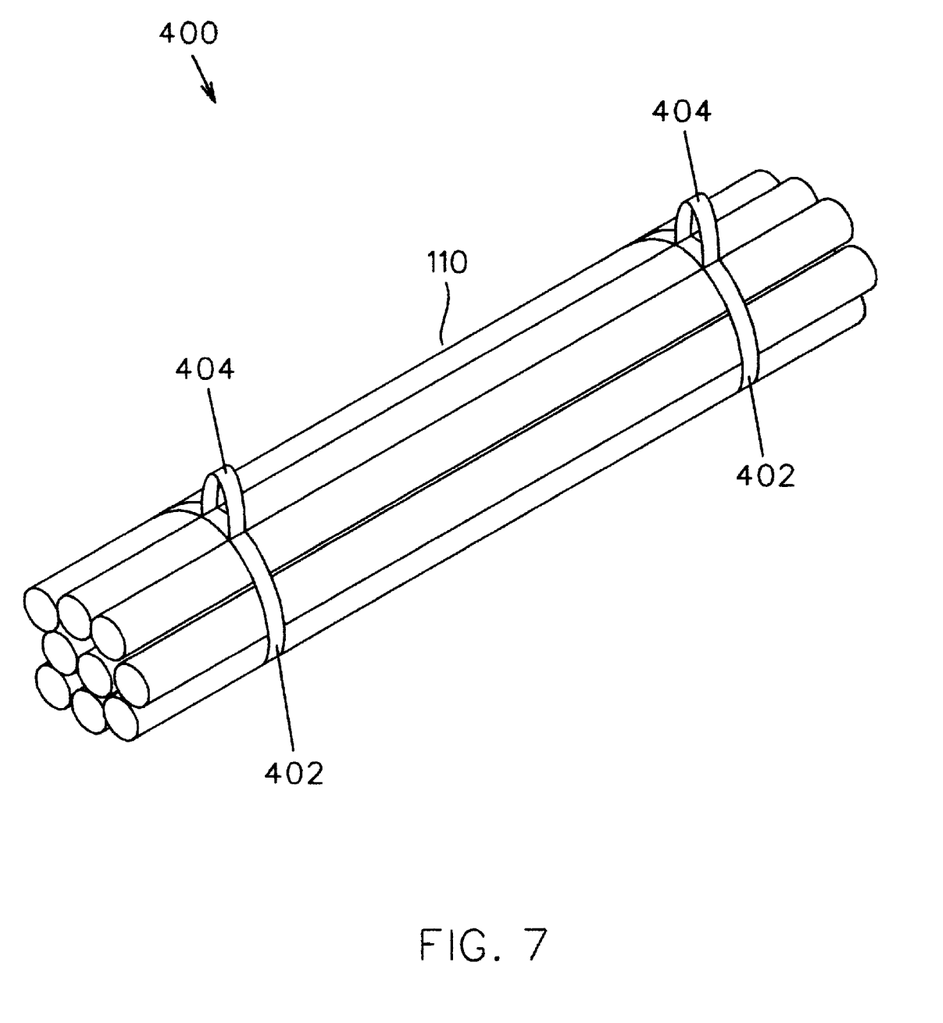
FIG. 7 is a perspective view of the apparatus of FIG. 6.

As shown in FIGS. 6 and 7, the tanning apparatus is collapsible into a compact bundle 400 for transport or storage. The apparatus is prepared for transport or storage first by laying the apparatus on the floor such that the rear panel 130 of each lamp housing 110 is in contact with the floor surface. Next, the apparatus 100 is rolled into a bundle 400 and secured with VELCRO® straps 402. The straps include handles 404 fixedly attached thereto for use in transporting the apparatus.

Accordingly, it can be seen that the home tanning apparatus is adaptable to provide a complete and efficient tan to a person who is either standing or lying down within a residential environment. Further, the tanning apparatus is lightweight and flexible so as to collapse into a compact bundle for transport or storage following use.

It is to be understood that while certain forms of this invention have been illustrated and described, it is not limited thereto except insofar as such limitations are included in the following claims and allowable functional equivalents thereof.

Having thus described the invention, what is claimed as new and desired to be secured by Letters Patent is as follows:

1. A tanning apparatus comprising:

a plurality of lamp housings, including an initial housing and terminal housing with a plurality of intermediate housings therebetween, each housing having a tanning lamp therein;

at least one channel extending along said initial housing and terminal housing;

a pair of spaced-apart channels extending along each intermediate housing;

a wall panel extending between adjacent housings of said plurality of housings between said initial and terminal housings, each end wall panel presenting first and second spaced apart edges for releasable insertion in adjacent channels of adjacent housings;

means for delivering electrical power to one of said housings for powering said lamp therein;

means for communicating said power from said one housing to said plurality of housings whereby to power said plurality of lamps, said plurality of housings with said walls extending therebetween positionable about a user for impingement of light from said tanning lamps on the user.

2. The apparatus as claimed in claim 1 wherein said delivering means comprises:

a power cord extending from said one of said housings for connection to a power source, and said communicating means comprises:

a plurality of supplemental power cords, each supplemental cord connected between adjacent housings in electrical series with said lamp therein and said one housing in connection with said power cord, said plurality of supplemental power cords communicating said power to said housings connected thereto.

3. The apparatus as claimed in claim 2 wherein said supplemental power cords are releasably connected to said housings.

4. The apparatus as claimed in claim 1 further comprising a reflective surface on at least one of said wall panels for dispersion of light emitted by said lamps onto a user.

5. The apparatus as claimed in claim 1 further comprising means at one end of a housing for maintaining said housing in a vertical position.

6. The apparatus as claimed in claim 5 wherein said maintaining means comprises a pedestal at said one end of said housing.

7. The apparatus as claimed in claim 1 wherein each housing includes an electrical socket for insertion of one end of said lamp therein, said electrical power directed to said socket by said power cord and said supplemental cords.

8. The apparatus as claimed in claim 2 wherein each housing includes an electrical socket for insertion of one end of said lamp therein, said electrical power directed to said socket by said delivering and communicating means.

9. The apparatus as claimed in claim 8 wherein each supplemental cord has opposed ends releasably engageable with said socket in adjacent housings.

10. The apparatus as claimed in claim 1 further comprising a frame adapted to overlie a recumbent user, said plurality of housings positioned about said frame in a manner to overlie the user.

11. The apparatus as claimed in claim 1 wherein said first housing is positioned adjacent said terminal housing with said housings in a vertical position, whereby to encircle a user.

12. The apparatus as claimed in claim 1 wherein each housing further includes a transparent cover releasable from said housing for allowing user access therein.

13. The apparatus as claimed in claim 1 wherein said wall panels are of a flexible material, whereby to allow for a variable positioning of each housing relative to an adjacent housing.

14. A tanning apparatus comprising:

a plurality of spaced-apart housings, each housing having a tanning lamp assembly therein, said plurality of housings comprising an initial housing and a terminal housing with intermediate housings therebetween;

means for delivering power to said housings for energizing each lamp assembly therein; and a wall panel for extension between adjacent housings of said plurality of housings;

means for releasably attaching each wall panel in said extension between adjacent housings of said plurality of housings, whereupon a placement of said housings about a user emits light from said energized tanning lamp assemblies thereon.

15. The apparatus as claimed in claim 14 wherein said attaching means comprises:

at least one channel extending along said initial and terminal housings, said at least one channel configured for engagement with a free edge of one of said wall panels;

a pair of spaced-apart channels on opposed sides of said intermediate housings, said channels configured for engagement with a free edge of a wall panel connected to adjacent downstream and upstream housings, whereby to extend said wall panels between adjacent housings.

16. The apparatus as claimed in claim 15 wherein said free edges of each wall panel are configured for releasable engagement within said respective channels of adjacent housings.

17. The apparatus as claimed in claim 14 wherein said delivery means comprises:

a power cord extending from one of said housings to a power source;

a plurality of supplemental power cords extending between adjacent housings and in series connection with said power cord, a delivery of power to said one housing communicated to said remaining housing through said supplemental power cords in series connection therewith.

18. A tanning apparatus comprising:

a plurality of lamp housings in an initial in-line relationship, including a first housing and terminal housing with at least one intermediate housing therebetween, each housing having a tanning lamp therein;

a flexible panel releasably attachable between adjacent housings in said in-line relationship;

means for delivering electrical power to each housing for powering each lamp therein, said plurality of lamp housings with said panels extending therebetween positionable about a user for impingement of light thereon.

19. The apparatus as claimed in claim 18 further comprising means for positioning said lamp housings in a vertical position, whereby to tan a user.

20. The apparatus as claimed in claim 18 further comprising means for supporting said lamp housings in a position about a recumbent user.

* * * * *

UNITED STATES PATENT AND TRADEMARK OFFICE
CERTIFICATE OF CORRECTION

PATENT NO. : 5,957,959
DATED : September 28, 1999
INVENTOR(S) : Pouran Rissmaney and David J. Hansen It is certified that error appears in the above-identified patent and that said Letters Patent is hereby corrected as shown below:

Column 4, line 55, delete "end".

Column 5, lines 21-25, delete claim 7.

Column 6, line 32, delete the second occurrence of "housing" and substitute --housings--.

Signed and Sealed this

Fourteenth Day of March, 2000

Attest:

Attesting Officer

Q. TODD DICKINSON

Commissioner of Patents and Trademarks